(12) United States Patent
Leyns et al.

(10) Patent No.: US 10,772,275 B2
(45) Date of Patent: Sep. 15, 2020

(54) METHOD AND APPARATUS FOR HIGH THROUGHPUT TESTING OF A TREATMENT ON ONE OR MORE CHARACTERISTIC OF PLANTS

(71) Applicant: BASF PLANT SCIENCE COMPANY GMBH, Ludwigshafen (DE)

(72) Inventors: Frederik Leyns, Oosterzele (BE); Joris Eeckhout, Maarkedal (BE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 69 days.

(21) Appl. No.: 16/098,282

(22) PCT Filed: Apr. 28, 2017

(86) PCT No.: PCT/EP2017/060275
§ 371 (c)(1),
(2) Date: Nov. 1, 2018

(87) PCT Pub. No.: WO2017/191065
PCT Pub. Date: Nov. 9, 2017

(65) Prior Publication Data
US 2019/0116749 A1    Apr. 25, 2019

Related U.S. Application Data

(60) Provisional application No. 62/332,769, filed on May 6, 2016.

(30) Foreign Application Priority Data

May 9, 2016    (EP) .................................... 16168766

(51) Int. Cl.
*A01H 3/04*    (2006.01)
*G01N 33/00*    (2006.01)
(Continued)

(52) U.S. Cl.
CPC ................ *A01H 3/04* (2013.01); *A01G 7/00* (2013.01); *G01N 33/0098* (2013.01);
(Continued)

(58) Field of Classification Search
CPC . A01G 9/00; A01G 2/00; A01G 22/60; A01G 13/0206
See application file for complete search history.

(56) References Cited

U.S. PATENT DOCUMENTS 6,921,182 B2 *   7/2005   Anderson, Jr.  ........ A01G 7/045
                                                  362/230
7,263,210 B2 *   8/2007   Kummel  ............. A01M 7/0089
                                                  382/110
(Continued)

FOREIGN PATENT DOCUMENTS

WO    WO-2010/031780 A1    3/2010
WO    WO-2013/001436 A1    1/2013
WO    WO-2015/043623 A1    4/2015

OTHER PUBLICATIONS

Hartmann et al., HTPheno: an image analysis pipeline for high-throughput plant phenotyping, BMC Bioinformatics, 12:148 (May 2011).

(Continued)

*Primary Examiner* — Yosef Kassa
(74) *Attorney, Agent, or Firm* — Marshall, Gerstein & Borun LLP

(57) ABSTRACT

The invention relates to a method and apparatus for evaluation of the effect of a treatment on one or more characteristics of a plant. More particularly, the invention relates to a method and apparatus for high throughput analysis of the effect of a treatment on one or more characteristics of a plant.

14 Claims, 7 Drawing Sheets

(51) Int. Cl.
*G06T 7/00* (2017.01)
*G01N 33/50* (2006.01)
*A01G 7/00* (2006.01)

(52) U.S. Cl.
CPC ....... *G01N 33/5097* (2013.01); *G06T 7/0012* (2013.01); *G06T 7/0016* (2013.01); *G06T 2207/10016* (2013.01); *G06T 2207/10024* (2013.01); *G06T 2207/30004* (2013.01)

(56) References Cited

U.S. PATENT DOCUMENTS

| | | | | |
|---|---|---|---|---|
| 7,472,513 | B2 * | 1/2009 | Bula | A01G 9/16 47/89 |
| 7,905,052 | B2 * | 3/2011 | Hurst | A01G 7/045 47/17 |
| 8,341,880 | B2 * | 1/2013 | Lejeune | A01G 9/00 47/58.1 R |
| 8,559,679 | B2 * | 10/2013 | Lejeune | A01G 7/00 382/110 |
| 2011/0135161 | A1 | 6/2011 | Koutsky et al. | |

OTHER PUBLICATIONS

International Application No. PCT/EP2017/060275, International Search Report and Written Opinion, dated Jun. 26, 2017.
Stanley et al., Methods for Rapid Screening in Woody Plant Herbicide Development, Forests, 5(7):1584-95 (Jul. 2014).
European Patent Application No. 16168766.0, Extended European Search Report, dated Nov. 2, 2016.

* cited by examiner

METHOD AND APPARATUS FOR HIGH THROUGHPUT TESTING OF A TREATMENT ON ONE OR MORE CHARACTERISTIC OF PLANTS

TECHNICAL FIELD

This invention relates to evaluation of the effects of treatment on one or more characteristics of plants.

More in particular, the invention relates to a method and apparatus for evaluation of the effects of a treatment on one or more characteristics of plants.

BACKGROUND ART

When growing plants, e.g. cultivated for their seeds (also called seed crops) for example rice, wheat, barley, corn, soybean, canola, sunflower, millet and safflower, a major goal is to support the growth of the plant such that they produce a high yield in e.g. seeds or biomass or roots. Farmers support this growth amongst others by application of fertilisers, herbicides, pesticides, insecticides, bactericides, nematicides and/or fungicides.

In the development of these chemicals and/or biologicals for application, such as fertilisers, herbicides, pesticides, insecticides, bactericides nematicides and/or fungicides, the testing of those products and the testing of the formulations comprising those products is an important step. The screening of the effects of the application of these products and their effective amounts is traditionally done in a field setting using large amounts of plants. Accelerated systems for screening herbicide treatments were already developed as described e.g. by Stanley et al. in *Forests* 2014, 5, 1584-1595.

Tools for fast, accurate and efficient screening for effects of chemical and/or biological treatment on plant are a necessity for the plant growing industry. But also other types of treatment might provide the plant growing industry further insights.

Traditional methods for evaluating the effect of treatment on plants comprise a phenotyping of the plants, which involve labour-intensive procedures such as manual and visual measurements of dimensions, such as above and belowground biomass, pigments, shapes, growth, counting of plant parts, and weighing of plant parts such as individual leaves, inflorescences and seeds. Some of these operations require detaching the plant parts of interest from the subtending plant organs. Advancements in the phenotyping of plants are already available e.g. as described in WO 2010/031780 or WO 2013/001436.

Disclosure of Invention

It is therefore an object of the present invention to provide a device and methods which at least partially avoid the disadvantages and shortcomings of the systems and methods known from the prior art.

The present invention overcomes these shortcomings by providing an apparatus and method for evaluation of the effects of a treatment on the physical characteristics of plants. In a preferred embodiment, the apparatus and method provide for a high throughput and fully automated evaluation of the effects of a treatment on one or more characteristics of plants.

The invention further relates to a method and apparatus for selecting the most desired genotypes based on scoring of one or more characteristics of treated plants, and to a method for rapid analysis of stress resistance of treated plant specimens. Biotic stress can be caused, for example, by bacterial, fungal, or viral disease, insects and nematodes. Abiotic stress can be caused, for example, by heat, drought, cold, wind, high salinity, and low or too high nutrient levels. The invention further relates to a method and apparatus to screen for a desired chemical or biological compound to treat a plant with, or a formulation thereof, or for determining the most optimal application regime of such chemical or biological compound, e.g. depending on the developmental stage of the plant. Examples of chemical compounds include fertilizers, herbicides, insecticides, pesticides, bactericides, nematicides, compounds inducing or inhibiting certain developmental steps in plant growth, and nutrients; examples of biological compounds include formulations comprising microorganisms or spores with a particular, preferably beneficial effect on plant growth (growth promotion, treatment of disease).

Devices and methods of this kind may be applied in all fields of agricultural research and commercial activities and in all fields of chemical and/or biological technology related to plants and plant specimens. Preferably, the device and methods according to the present invention may be applied to the technical field of testing of plants, testing of chemical or biological compounds and/or testing of methods for treatment of plants, such as one or more of: testing and/or evaluation of foliar application of biologicals and/or chemicals; testing of resistance of treated plants against specific types of stress; testing of specific fertilizers, herbicides, insecticides, pesticides, bactericides, nematicides and/or nutrients; the testing of the effect and/or effectiveness of specific treatment regimes, such as 1, 2, 3, 4, 5, 6, 7, 8, 9, 10, 11, 12, 13, 14, 15, 16, 17, 18, 19, 20 treatments of the plants or plant specimens with fertilizers and/or biocides. However, other applications of the present invention are possible.

Here, we describe a method and apparatus for analysis of the effects of a treatment on one or more characteristics of plants, which enhances dramatically the statistical power of the evaluation compared to traditional automated methods based on the "first in-last out" or "first in-first out" principles, because it provides for a real randomisation of the plants thereby reducing position and/or edge effects (i.e. effects on plant growth caused by a particular position at the growing location). The method and apparatus described herein enable a high throughput analysis of plants as these enable continuous processing and treatment of the provided plants. Preferably, the methods and apparatus of the present invention comprise a fully automated imaging and image processing step.

Further advantages of the invention will become apparent from the following description.

Plants that can be evaluated by the present method and apparatus can be any plant or population having similar or differing genetic information. These plants may be different varieties, hybrids, inbreds and transgenic plants.

An aspect of the present invention provides a method for high throughput evaluation of the effects of a treatment on a plurality of plants.

The method comprises following steps: a plurality of plant containers wherein at least one plant is growing is provided as well as a container moving system to move said plant containers. A pre-treatment randomisation system is provided to randomise the order of said plant containers. And also a treatment system and a post-treatment randomisation system are provided. Each of said plant containers are moved by said container moving system to the pre-treatment randomisation system wherein the order of the plant containers are randomised. Thereafter the container moving system moves the containers to the treatment system, the treatment system then providing at least one treatment. Thereafter, the containers are moved by the container moving system to the post-treatment randomisation system wherein the order of the plant containers are randomised for a second time. Thereafter, the containers are moved by container moving system to a growing location. The post-treatment randomisation step assures that position or edge effects from the growing location on the groups of treated plants are minimised. The effect of the at least one treatment is then evaluated in a next step, at one or more timepoints after treatment.

The treatment in the above method can be any treatment a plant can undergo. Such treatment can be one or more of a foliar treatment, e.g. foliar treatment with a chemical or biological solution or powder, a foliar treatment with a coating solution or powder, a foliar treatment with a marker solution or powder; watering with a specified solution, such as nutrient solution and/or biocide solution; heating and/or cooling the plant in the plant container; providing a light application; shaking the plant container; a blowing application on the plant; raining and/or snowing and/or hailing application; high pressure or low pressure atmospheric environment application; fumigation or a gaseous application; or a sound or sonic treatment. Other treatments can also be a pollination action, or a hormonal application, or an inoculation, and/or insect and/or microbial and/or fungal infestation application.

Plants in a greenhouse are influenced by variations in the growth environment caused by variations in, for example, temperature, humidity, light, nutrient, and water supply, which are dependent on the location of the plant in the greenhouse. A plant at the outer side of the greenhouse is exposed to a different micro-environment than a plant at the centre of the greenhouse. Typically, the plants are set-up in plant containers in rows or on tables in such greenhouse and problems of environment-associated phenotype and/or metabolite components are dealt with by moving the plant containers to another spot in the greenhouse. Most of the commercially available systems work, in case of a row set-up, in a first-in, first-out or a first-in, last out way. This is not providing a real randomisation of the plants or plant containers. This is overcome by the system and method of the invention. The advantage of the method and apparatus of the invention is that the pre-treatment randomisation uses the originating cultivation location as the randomising factor and that the post-treatment randomisation uses the treatment as the randomising factor. This first randomisation averages the effect of the growing location before treatment and the second randomization after treatment will randomize the treated plants again such that the later measurement of the one or more characteristics will be done on truly randomized plants which are, after treatment, also growing at a cultivation location having its specific micro-environment. In addition, where a heterogenous population of plants are grown (e.g. a population of plants having different genotypes, a population of plants after a mutagenesis treatment or a set of transgenic events) a further randomisation is possible at the sowing or planting stage, to minimize position or edge effects from the growing location.

The treatment is preferably done on a group of several plants being subjected to the same treatment (a block). As such the method of the invention provides for a fully automated system to perform randomized block trials to test the effect of a specific treatment or to identify the best performing treatment for a desired or undesired effect out of a group of treatments; e.g. a foliar application with the same substance in differing dilutions.

In a preferred embodiment, the method of the invention is a high throughput evaluation of the effects of a foliar treatment, preferably a spraying, comprising the steps as provided above. In an even more preferred embodiment, the method then also provides a drying system wherein the plant containers pass the drying system after the spraying treatment. In another preferred embodiment, the treatment is a watering of the plant container with a defined solution, e.g. a defined nutrient solution or a defined biocide solution.

Preferably, each plant is linked to a unique identifier. Preferably, the identifier may be or may comprise, but is not limited to, one or more of the following identifiers: a barcode; a contactless electronic identifier, i.e. an identifier comprising at least one piece of information, which may be read from the identifier, preferably without any physical contact between a reading mechanism, preferably a reader, and the identifier, most preferably the identifier may be at least one radio frequency identification tag (RFID tag). However, alternatively or additionally, other types of identifiers are possible. The information may be a simple identification, e.g. a plant specimen and/or a genotype and/or growth conditions and/or treatment. In general, the at least one identifier not necessarily has to be in physical contact with the plant, but should be assigned to a respective plant in any unambiguous way.

The evaluation can be done by visual scoring or by sampling or by imaging.

Preferably, the method further provides at least one imaging system. The plant containers than also pass through this imaging system while performing the method. Imaging can be done before and/or after the treatment. Preferably, the evaluation of the effect of the treatment is made by use of this imaging system. Such evaluation of the effect of the treatment is preferably done when the plants had some time to obtain the full effect of the treatment. In the case of a foliar application, the evaluation is preferably done after the plants had the chance to grow in the randomised block pattern on the growing location. The plants can then be imaged by use of the imaging system of the method.

Preferably, the imaging system comprises at least one detector.

The term detector, as used in the present invention, may imply any type of detector, preferably a detector for electromagnetic waves. The term electromagnetic radiation, as used in the present invention, may comprise light in the visible range, X-ray, UV, infrared and near-infrared, thermal and terahertz radiation. It may comprise monochromatic electromagnetic (EM) radiation as well as a broad spectrum EM-radiation and it may comprise incoherent EM-radiation as well as coherent EM-radiation, polarised and unpolarised EM-radiation. Other types of electromagnetic waves are also possible. More preferably the detector may comprise a detector for light in at least one spectral wave length region selected from a visible, an infrared and ultraviolet wavelength region and most preferably a camera. The camera may be a digital camera, preferably with spatial and/or time resolution.

Preferably, the detector acquires at least one spatially resolved image. One or more characteristics are then measured from said image by appropriate software which then provides resulting information.

Preferably, the imaging system is imaging one or more characteristic of each of the plants. The imaging system then also provides for analysing the images for the one or more characteristic of each of the plants by computer processing and for associating the resulting information with the unique identifier information for each of the plants respectively.

In an even more preferred embodiment, the method also comprises a step of directing electromagnetic waves to the plant, such that the plant emits or reflects electromagnetic waves. The plant is then imaged by the detector at different wavelengths wherein images comprising pixels are obtained. These images recorded at different wavelengths are aligned on the basis of the pixels, such that a 3-dimensional image is generated. The 3-dimensional image, the image cube, comprises 2 spatial dimensions and 1 spectral dimension. In the next step of this method, a customary predictive mathematical model combining the weighted contributions of the different wavelengths is used to obtaining a multispectral or hyperspectral imaging cube of the plant and the one or more characteristics is then measured from said imaging cube by appropriate software.

The electromagnetic waves emitted or reflected from the plant are preferably transmitted light. In another preferred embodiment, the electromagnetic waves emitted or reflected from the plant are reflected light.

In a preferred embodiment the images are collected at many different narrow wavebands in the near infrared range of the light spectrum, preferably between 900 and 1800 nm.

In an even more preferred embodiment, the method comprises the hyperspectral or multispectral imaging described above in combination with a 3D imaging, which provides a 4-dimensional image.

The term image, as used in the present invention, may imply any type of images, preferably at least two-dimensional images. The images may be optical images. The images may comprise transmission images and/or shadow images and/or reflection images. The images may be generated by detecting an emission signal, e.g. a fluorescence and/or phosphorescence signal. Thus, the images may be generated by chlorophyll fluorescence measurements and/or selectable marker fluorescence measurements. The signal which may be used to generate an image may be discrete in time or may be a continuous signal. Other types of images are also possible as e.g. described hereunder. From the above it follows that the term imaging, as used in the present invention, may imply any way of acquiring images. The one or more characteristics are measured from the image by appropriate software. If desired, algorithms may be used to evaluate the measured one or more characteristics.

In a preferred embodiment, the imaging system images plants while the plants are being moved and turned at the same time in a controlled manner to be able to take images of all sides of the plant and store them in digital format, for example as described in WO 2010/031780. By turning the plants while imaging them, an additional step of orienting the plant with its maximal radial axis towards the imaging device can be avoided, and a more complete picture of the plant is obtained.

The one or more characteristics comprise one or more of, but are not limited to, an observable physical manifestation of the plant, a phenotypic trait, metabolic trait, colour, greenness, yield, growth, biomass, maturity, a transgenic trait, flowering, nutrient use, water use, or effects of disease, pests, and/or stress. Preferably, the one or more characteristics comprise one or more of area, height, width, leaf angle, number of leaves, presence and/or number of inflorescences, number of shoots, and branching pattern. In another preferred embodiment, the one or more characteristics comprise one or more of different metabolites, and might entail the assessment of the presence or absence of a specific metabolite, number of metabolites, the amount of a specific metabolite, . . . .

In a preferred embodiment, the methods of the present invention can be used to detect any characteristic of the plants that can be measured by imaging. The images may be taken from aboveground plant parts and/or or plants roots. The aboveground plant parts may be one or more of shoots, leaves, tillers, inflorescence, flowers, seeds. In one preferred embodiment, the one or more characteristic is one or more of a quantitative trait, a biochemical trait and a morphological trait. In an even more preferred embodiment, the biochemical trait is selected from the group comprising of oil composition, protein composition, carbohydrate composition, fibre composition, oil content, protein content, carbohydrate content, starch content, fibre content, dry weight and water content. In another even more preferred embodiment, the morphological trait is selected from plant architecture, plant size, plant shape, aboveground biomass, plant colour, plant growth rate, leaf surface texture, plant weight, plant integrity, leaf integrity, leaf colour, leaf shape, leaf size, leaf growth rate, belowground biomass, root growth rate, root thickness, root length, root anchorage, inflorescence architecture, flower size, flower shape, flower colour, flower surface texture, flower weight, flower integrity, endosperm size, germ size, seed shape, seed size, seed colour, seed surface texture, seed weight, seed density, and seed integrity. As used herein, integrity is correlated to susceptibility or resistance to any one of diseases, insect infestation, fungal infestation or environmental stress. In an alternative preferred embodiment, the quantitative trait is selected from amount of (green) leaves, amount of roots, such as amount of hairy roots and/or branched roots, amount of florets, amount of seeds, amount of empty seeds, amount of branching, weight of seeds, total weight of seeds and/or fill rate. However, other types of parameters and/or combinations of the named parameters and/or other parameters may be possible, e.g. aboveground biomass per plant and per area; belowground biomass per area; content of oil, starch and/or protein in aboveground biomass (e.g., seeds or vegetative parts of the plant); number of flowers (florets) per plant; or modified architecture, such as increase stalk diameter, thickness or improvement of physical properties (e.g. elasticity, soil penetration capacity of roots). Where applicable, changes in characteristics of the plants can be measured over time or by comparison to suitable control plants such as wild-type or reference plants, or untreated plants. Untreated plants can for example be plants that received no treatment at all, or that were treated, in case of spraying, with water only or with the formulation in absence of the active ingredient(s). Persons skilled in the art are aware of selecting proper control plants.

In another preferred embodiment, the methods of the present invention can be used to detect any characteristic of the plants that can be measured by taking a small sample of the plants. The sample can be taken from any part of the plant, such as aboveground parts, such as a leaf or a flower, or from belowground parts, such as roots or root microbiome. The samples are then analysed by metabolic profiling for one or more characteristics.

In a preferred embodiment, the method further comprises a step of analysing the resulting information for the one or more characteristic for the one or more plant(s) to determine the impact of the treatment.

The methods of the present invention can be used to analyse the impact of genetic modifications on plants in combination with the evaluation of the effects of a treatment, and in particular on one or more characteristics of the plant, and selecting a plant with a genetic modification of interest. Such method comprises following steps: first a plurality of plants with differing genotypes are grown. Preferably each plant is associated with an identifier, more preferably a machine readable identifier that distinguishes the plant from other plants. Plants are treated and images or samples are obtained using the methods described herein and these images or samples are then analysed for one or more characteristic, and/or trait as described above, to determine the impact of the treatment in relation to the genetic modification. A selection can then be made for a plant or seeds thereof with a genetic modification of interest in relation to the treatment. If desired, algorithms may be used to select and evaluate the measured one or more characteristics and the results statistically analysed to identify plants with genetic modifications of interest, for selecting the best performing candidates or for selecting candidates having any given characteristics for any given further treatment.

The creation of genotypic variation can be based on genetic modifications made in the lab, but can also rely on the production of genetic alterations that can be obtained by techniques including recombination through classical crossing, chemical mutagenesis, radiation-induced mutation, somatic hybridisation, inter-specific crossing and genetic engineering. The obtained plants can be compared to other non-transgenic plants, to transgenic plants and/or to corresponding control plants. Following the creation of genotypic variation, selection of those genotypes having the most desirable agronomic one or more characteristics is performed.

The information resulting from the measurement of the one or more characteristics from the image or sample by appropriate software is preferably also associated to the identifier.

The invention provides in another of its aspects a process for evaluating and recording of the effects of a treatment on one or more characteristics of a plant, comprising the steps of identifying the plant, treating and imaging the plants using the methods described herein, determining the one or more characteristics and recording results in a prescribed format in a computer database together with the plant identifier.

The computer database compiled by subjecting plants to a process as aforesaid may be interrogated and enables rapid comparison of characteristics from a multitude of different plants and thus permits rapid determination of seeds from which further plants may be derived which yield seeds having desired characteristics.

The invention provides in another of its aspects a process for comparing one or more of the characteristics of the plants in a batch of treated plants with corresponding characteristics of batches of plants subjected to another treatment, in which a computer database compiled by subjecting batches of plants to a process according to the last preceding paragraph but one is interrogated concerning said one or more characteristics.

Likewise, the computer database compiled by subjecting plants to a process as aforesaid may be interrogated and enables rapid comparison of characteristics from a multitude of different plants and thus permits rapid determination of compounds with which the plants were treated and which compounds have desired characteristics. Such compounds can be chemical compounds or biological compounds. In a similar way, the computer database can be interrogated to determine optimal dosing or treatment regimes, dependent on how the treatment of the plants was set up. The invention thus provides in another of its aspects a process for comparing one or more chemical or biological compounds having effect on the characteristics of plants in a batch of treated plants when compared to corresponding characteristics of batches of untreated plants or of plants subjected to another treatment.

Preferably, the method further provides for a step wherein one or more plants are selected for further use in a plant breeding or advancement experiment or for introducing further modifications in transgenic plants. Likewise, the method further provides for a step wherein one or more compounds are selected for further use in an advancement experiment, or wherein a dosing or treatment regime is further optimised. Examples of advancement experiments include further optimisation experiments, or further selection experiments, further screening experiments and the like.

Another aspect of the invention provides an apparatus for high-throughput application of a treatment on a plurality of plant containers wherein at least one plant is growing, wherein the apparatus comprises a container moving system to move the plant containers; a pre-treatment randomisation system to randomise the order of the plant containers; a treatment system; and a post-treatment randomisation system. Each of the plant containers move into the apparatus by the container moving system and to the pre-treatment randomisation system. The plant containers are then randomised by that pre-treatment randomisation system, where after the containers move further on the container moving system to the treatment system which then treats the plants in the plant containers. Thereafter, the plant containers move via the container moving system to the post-treatment randomisation system which performs a second randomisation of the plant containers. Thereafter the plant containers are moved out of the apparatus by the container moving system. Preferably, the plant containers are then moved to a plant growing location, such as a greenhouse or screenhouse.

The treatment in the above apparatus can be any treatment a plant can undergo. Such treatment can be one or more of a foliar treatment; watering with a specified solution, such as nutrient solution and/or biocide solution; heating and/or cooling the plant in the plant container; providing a light application; shaking the plant container; a blowing application on the plant; raining and/or snowing and/or hailing application; high pressure or low pressure atmospheric environment application; fumigation or a gaseous application, or a sound or sonic treatment. Other treatments can also be a pollination action, or a hormonal application, or an inoculation, and/or insect and/or microbial and/or fungal infestation application. Typically, the treatment is used in a screening program, where for example one or more plants are tested for a response to the treatment, or where one or more chemical compounds or one or more biological agents are tested for their effect on plants or on plant growth.

The treatment is preferably done in a block of several plants being subjected to the same treatment. As such the apparatus of the invention provides for a fully automated system to perform randomized block trials to test the effect of a specific treatment or to identify the best performing treatment for a desired or undesired effect out of a group of treatments; e.g. a foliar application with the same substance in differing dilutions or differing formulations. The post-treatment randomisation step will randomly distribute the plant containers with the treated plants over the growing location, thereby minimising position or edge effects of the growing location.

In a preferred embodiment, the apparatus of the invention enables a high throughput evaluation of the effects of a foliar treatment, preferably a spraying, comprising the steps as provided above. In an even more preferred embodiment, the apparatus also provides a drying system wherein the plant containers pass the drying system after the spraying treatment.

In another preferred embodiment, the treatment is a watering of the plant container with a defined solution, e.g. a defined nutrient solution or a defined biocide solution.

The apparatus may further also comprise one or more identifier reader(s) to identify an identifier linked to the plant in the plant container, the reader preferably providing output in digital form. Examples of such a reader are, but are not limited to, a barcode reader, a transponder reader and an RFID reader. In a preferred embodiment, the apparatus further comprises at least one electronic code reading device to identify an identifier linked to said plant. The identifier reader is preferably integrated by use of software in a computer device and fed therefrom to the database. The database may be manipulated to inspect and compare data to determine various characteristics of the plant. The apparatus preferably comprises as many identifier readers as needed to be able to determine the identity of a plant at any position in the apparatus: before and/or after the pre-randomisation stage, at the treatment stage, before and/or after the post treatment randomisation stage.

In another preferred embodiment, the apparatus comprises also at least one imaging system. Preferably, the imaging system comprises one or more detectors. Even more preferably, the imaging system comprises at least one detector, most preferably at least one digital camera. The term detector, as used in the present invention, may imply any type of detector, preferably a detector for electromagnetic waves. The term electromagnetic waves, as used in the present invention, may comprise light in the visible range, infrared and near-infrared light. It may comprise monochromatic light as well as a broad spectrum of light and it may comprise incoherent light as well as coherent light. Other types of electromagnetic waves are also possible. More preferably the detector may comprise a detector for light in at least one spectral wave length region selected from a visible, an infrared and ultraviolet wavelength region and most preferably a camera. The camera may be a digital camera, preferably with spatial and/or time resolution. More preferably, the camera is a line scan camera.

In a preferred embodiment, the treatment system and the imaging system can operate independent from each other or they can co-operate, thus giving the apparatus a great versatility: for example, plants can be moved from the growing location to the imaging system for analysis, and subsequently moved back to the growing location, or plants can be moved from the growing location to the treatment system for treatment and subsequently moved back to the growing location, or plants can be moved from the growing location to the imaging system for analysis, and subsequently moved to the treatment system for treatment (or vice versa) and subsequently moved back to the growing location. The apparatus thus allows one set of plant containers being imaged in the imaging system and another set of plant containers simultaneously being treated in the treatment system without interfering with each other.

The apparatus may further comprise at least one image analysis device. The image analysis device may be adapted to perform at least one image analysis of at least one of the images, preferably the image analysis device may be adapted to derive at least one characteristic of the plant. The one or more characteristics are measured based on analysis of the image by appropriate software. If desired, algorithms may be used to evaluate the measured one or more characteristics.

The apparatus further may have at least one database for recording data regarding the plants and the treatment or treatments performed on each plant. The data preferably may be at least one of the following: at least one image of the plant; at least one or more characteristics or trait derived from at least one image of the plant; information from the identifier; treatment performed on the plant. As outlined above, the at least one characteristic or trait may comprise one or more parameters characterizing the characteristic or trait of the plant.

The one or more characteristics comprise one or more of an observable physical manifestation of the plant, a phenotypic trait, a metabolic trait, colour, greenness, yield, growth, biomass, maturity, a transgenic trait, flowering, nutrient use, water use, or effects of disease, pests, and/or stress. Preferably, the one or more characteristics comprise one or more of area, height, width, leaf angle, number of leaves, presence and/or number of inflorescences, number of shoots, and branching pattern.

In a preferred embodiment, the apparatus of the present invention can be used to detect any characteristic of the plants that can be measured by imaging. The images may be taken from aboveground plant parts and/or or plants roots. The aboveground plant parts may be one or more of shoots, leaves, tillers, inflorescence, flowers, seeds. A system for root imaging is described in WO 2010/031780.

In another preferred embodiment, the apparatus of the present invention can be used to detect any characteristic of the plants that can be measured by taking a small sample of the plants. The sample can be taken from any part of the plant, such as aboveground parts, such as a leaf or a flower, or from belowground parts, such as roots or root microbiome. The samples are then analysed for example by metabolic profiling for one or more metabolic characteristics, or by microbial analysis to determine the presence or absence of certain microorganisms, or for morphologic analysis on tissue or cellular level.

The at least one characteristic or trait may preferably be chosen from: one or more of a quantitative trait, a biochemical trait and a morphological trait. In a preferred embodiment, the biochemical trait is selected from the group consisting of oil composition, protein composition, carbohydrate composition, fibre composition, oil content, protein content, carbohydrate content, starch content, fibre content, dry weight and water content. In another preferred embodiment, the morphological trait is selected from plant architecture, plant size, plant shape, aboveground biomass, plant colour, plant growth rate, leaf surface texture, plant weight, plant integrity, leaf integrity, leaf colour, leaf shape, leaf size, leaf growth rate, belowground biomass, root growth rate, root thickness, root length, root anchorage, inflorescence architecture, flower size, flower shape, flower colour, flower surface texture, flower weight, flower integrity, endosperm size, germ size, seed shape, seed size, seed colour, seed surface texture, seed weight, seed density, and seed integrity. As used herein, integrity is correlated to susceptibility or resistance to any one of diseases, insect infestation, and fungal infestation.

In an alternative preferred embodiment, the quantitative trait is selected from amount of (green) leaves, amount of roots, such as amount of hairy roots and/or branched roots, amount of florets, amount of seeds, amount of empty seeds, amount of branching, weight of seeds, total weight of seeds and/or fill rate. However, other types of parameters and/or combinations of the named parameters and/or other parameters may be possible, e.g. aboveground biomass per plant and per area; belowground biomass per area; content of oil, starch and/or protein in aboveground biomass (e.g., seeds or vegetative parts of the plant); number of flowers (florets) per plant; or modified architecture, such as increase stalk diameter, thickness or improvement of physical properties (e.g. elasticity).

In another preferred embodiment, the one or more characteristics comprise one or more of different metabolites, and might entail the assessment of the presence or absence of a specific metabolite, number of metabolites, the amount of a specific metabolite, . . . .

The apparatus according to the invention permits derivation of data about plant characteristic(s) or traits after treatment without human intervention other than perhaps providing the treatment to the plants. It may be used for a variety of purposes and is especially useful for evaluation of biocides, such as foliar application of herbicides in differing dilutions. In such use, the apparatus provides an integrated automatic process for evaluating one or more characteristic and/or phenotype of a treated plant or plants. By use of the apparatus one may derive in a single operation desired data about key parameters of interest to the plant breeder such as optimal dilution of a specific compound or effective amounts of a compound, or optimal formulation of a specific compound. Other purposes for which the apparatus can be used include evaluation of growth promoting substances, in the form of a chemical compound or as a microbial suspension.

The apparatus furthermore may comprise a control system which may be adapted to control and/or to drive the imaging system and/or transporter and/or the conveyor belt systems and/or the image analysis device and/or the reader and/or the database and/or a power supply. The control system may comprise a computer and electrical and/or signal connectors, preferably electrical lines and interfaces.

Preferably, the imaging system is shielded from natural daylight. Light inside the imaging system may be provided by a standardized set of lamps of which the intensity can be controlled.

Images taken in the imaging system can be processed on-line using imaging analysis software to extract information on the plants and preferably, the processed data as well as the images get linked to the unique identifier of the corresponding plant and even more preferably, downloaded to a computer.

In a preferred embodiment, the imaging system comprises the following:
  at least one digital camera with sensitivity in the visual, infrared and/or near-infrared range;
  at least one spectrograph composed of an optical dispersing element such as a grating or prism to split the light into many narrow, adjacent wavelength bands, said spectrograph being placed before the camera and being tunable so that specific wavebands can be selected and transmitted to the camera in a predetermined sequence;
  at least one suitable optical lens;
  at least one light source with suitable spectral composition in the near infrared range to illuminate said plant,
  computer hardware elements and connections to the different previous elements and
  dedicated software elements for driving signal outputs and inputs from and to the hardware elements, and automatically perform the different steps of the method described herein.

Such imaging is often referred to in literature as imaging spectroscopy, which is the simultaneous acquisition of spatially co-registered images in many spectrally contiguous bands. The image produced by such imaging spectroscopy is similar to an image produced by a digital camera, except each pixel has many bands of light intensity data instead of just three bands: red, green, and blue. In the art, the wording "hyper spectral" data sets are described as being composed of relatively large number (e.g., 100-1000) spectral bands of relatively narrow bandwidths (e.g., 1-10 nm), whereas, "multi-spectral" data sets are usually fewer (e.g., 5-10) bands of relatively large bandwidths (e.g., 70-400 nm).

In a preferred embodiment, the imaging system comprises a hyperspectral camera. In another preferred embodiment, the imaging system comprises a multispectral camera.

Another aspect of the present invention provides for the use of an apparatus as described herein for evaluating the effects of a treatment on a plurality of plants. Preferably, such an apparatus is used in the methods as described herein.

In another aspect, the apparatus as described herein can be used in a method for comparing the effects of different treatments on similar plants.

In another aspect, the apparatus as described herein can be used in a method for comparing the effects of different growth conditions of plants in relation to the effects of a treatment on a plurality of plants.

In another aspect, the apparatus as described herein can be used for screening a population of plants by measuring the effects of a treatment, for example in a breeding experiment.

In another aspect, the apparatus as described herein can be used in a method for testing the effects of treatment of plants, such as one or more of: testing of specific fertilizers and/or nutrients; testing of specific pesticides, the selection and/or breeding of plants having one or more desired properties in response to the effects of a specific treatment; the testing of the effect and/or effectiveness of specific treatments, such as 1, 2, 3, 4, 5, 6, 7, 8, 9, 10, 11, 12, 13, 14, 15, 16, 17, 18, 19, 20 treatments of the plants or plant specimens with fertilizers, nutrients and/or biocides.

In an alternative aspect, the apparatus as described herein can be used in a method for phenotyping and/or metabolic profiling in relation to a treatment, for selecting the most desired genotypes based on phenotype and/or metabolic profile scoring of the treated plant.

In another alternative aspect, the apparatus as described herein can be used in a method for analysis of stress resistance of treated plant specimens.

SUMMARIZING THE IDEAS OF THE PRESENT INVENTION, THE FOLLOWING EMBODIMENTS ARE PREFERRED

Embodiment 1

Method for high throughput evaluation of the effects of a treatment on a plurality of plants said method comprising following steps:
  providing a plurality of plant containers 120 wherein at least one plant 121 is growing
  providing a container moving system 130 to move said plant containers
  providing a pre-treatment randomisation system 140 to randomise the order of said plant containers
  providing a treatment system 150, and
  providing a post-treatment randomisation system 160,
  wherein each of said plant containers 120 moves by said container moving system 130 to said pre-treatment randomisation system 140, said pre-treatment randomisation system 140 randomising the order of plant containers 121, said container moving system 130 then moving said containers 121 to said treatment system 150, said treatment system 150 providing at least one treatment, thereafter said container moving system 130 moving said containers to said post-treatment randomisation system 160, said post-treatment randomisation system 160 performing a second randomisation of the order of said plant containers, said container moving system 130 moving said containers 120 to a growing location and subsequently evaluating the effect of said treatment.

Embodiment 2

Method according to embodiment 1, wherein said plant in said plant container is linked to a unique identifier 180.

Embodiment 3

The method according to any one or more of the previous embodiments, said method further providing at least one imaging system 190, wherein said plant containers pass through said imaging system.

Embodiment 4

The method according to the previous embodiment, wherein said plant containers pass through an imaging system 190 before and/or after said treatment.

Embodiment 5

Method according to any one or more of the embodiments 3 or 4, wherein said evaluation of the effect of said treatment is made by use of said imaging system 190.

Embodiment 6

The method according to any one or more of the previous embodiments, wherein said imaging system comprises one or more detectors 191.

Embodiment 7

The method according to the previous embodiment, wherein said detector comprises a camera, preferably a digital camera.

Embodiment 8

Method according to any one or more of the previous embodiments 3 to 7, said imaging system 190 further providing:
directing electromagnetic waves on said plant thereby forming emitted or reflected electromagnetic waves from said plant;
imaging said plant at different wavelengths by said detector 191 thereby obtaining images comprising pixels;
aligning said images recorded at different wavelengths on the basis of said pixels, thereby generating a 3-dimensional image, said 3-dimensional image comprising 2 spatial dimensions and 1 spectral dimension;
using a customary predictive mathematical model combining the weighted contributions of the different wavelengths, thereby obtaining a multispectral or hyperspectral imaging cube of said plant;
measuring one or more characteristic from said imaging cube by appropriate software.

Embodiment 9

The method according to the previous embodiment, wherein said images are collected at many different narrow wavebands in the visual, infrared and/or near infrared range of the light spectrum, preferably between 900 and 1800 nanometres.

Embodiment 10

Method according to any one or more of embodiments 6 to 9, wherein said detector acquires at least one spatially resolved image, the method further providing for measurement of one or more characteristic from said image by appropriate software providing resulting information.

Embodiment 11

The method according to any one or more of the previous embodiments 3 to 10, wherein said imaging system 190 is imaging one or more characteristic of said plant and analysing the images for the one or more characteristic of the plant by computer processing and associating the resulting information with the unique identifier 180 information for said plant 121.

Embodiment 12

Method according to any one or more of embodiments 9 to 11, wherein the one or more characteristic comprises one or more of an observable physical manifestation of the plant, a phenotypic trait, metabolic trait, colour, greenness, yield, growth, biomass, maturity, a transgenic trait (i.e. a trait altered by the presence of a transgene), flowering, nutrient use, water use, or effects of disease, pests, and/or stress.

Embodiment 13

Method according to the previous embodiment, wherein said one or more characteristic is one or more of a quantitative trait, a biochemical trait and a morphological trait.

Embodiment 14

Method according to any one or more of the embodiments 8 to 12, wherein the one or more characteristic comprises one or more of area, height, width, leaf angle, number of leaves, presence and/or number of inflorescences, number of shoots, and branching pattern.

Embodiment 15

Method according to any one or more of embodiments 8 to 12, said method further comprising a step of analysing the resulting information for the one or more characteristic of the one or more plant(s) to determine the impact of the treatment.

Embodiment 16

The method of embodiment 1, wherein the plurality of plants comprise one or more transgenic plants.

Embodiment 17

The method of embodiment 1, wherein one or more plants are selected for further use in a plant breeding or advancement experiment or for introducing further modifications.

Embodiment 18

The method of embodiment 7, wherein the images and/or information are taken of above ground plant parts and/or of plant roots.

Embodiment 19

The method of embodiment 18, wherein the above ground plant parts comprise shoots, leaves, tillers, inflorescence, flowers, seed, or any combination thereof.

Embodiment 20

Method according to any or more of the previous embodiments, wherein the treatment is a foliar spraying treatment.

Embodiment 21

Method according to the previous embodiment, said method further providing a drying system 170, said method further comprising a step wherein the plant containers pass a drying system after the foliar spraying treatment.

Embodiment 22

Method according to any one or more of the embodiments 1 to 19, wherein the treatment is a watering of the plant container with a defined solution.

Embodiment 23

Method according to the previous embodiment, wherein the defined solution is a defined nutrient solution.

Embodiment 24

Method according to embodiment 22, wherein the defined solution is a defined biocide solution.

Embodiment 25

Apparatus for high throughput application of a treatment on a plurality of plant containers 120 wherein at least one plant 121 is growing, said apparatus comprising:
- a container moving system 130 to move said plant containers;
- a pre-treatment randomisation system 140 to randomise the order of said plant containers
- a treatment system 150, and
- a post-treatment randomisation system 160,
- wherein each of said plant containers 120 moves into said apparatus by said container moving system 130 to said pre-treatment randomisation system 140, the order of plant containers being randomised by said pre-treatment randomisation system 140 before moving further on said container moving system 130 to said treatment system 150 wherein said plant containers 120 are treated, the plant containers 120 then move via the container moving system 130 to the post-treatment randomisation system 160, the post-treatment randomization system 160 providing a second randomisation of the order of said plant containers and
- thereafter the plant containers 120 being moved by said container moving system 130 out of said apparatus.

Embodiment 26

Apparatus according to the previous embodiment, wherein said apparatus further comprises a unique identifier reader 181.

Embodiment 27

Apparatus according to any one or more of the embodiments 25 or 26, said apparatus further comprising at least one imaging system 190.

Embodiment 28

Apparatus according to the previous embodiment, wherein said imaging system 190 comprises one or more detectors 191.

Embodiment 29

Apparatus according to the previous embodiment, wherein said imaging system comprises at least one detector, preferably at least one digital camera.

Embodiment 30

Apparatus according to any one or more of the embodiments 25 to 29, wherein said treatment system 150 comprises a foliar spraying system 151.

Embodiment 31

Apparatus according to the previous embodiment, wherein said apparatus further comprises a drying system 170.

Embodiment 32

Apparatus according to any one or more of the embodiment 25 to 29, wherein said treatment system 150 comprises a watering system 152.

Embodiment 33

Apparatus according to any one or more of embodiments 27 to 32, wherein said imaging system 190 comprises:
- at least one digital camera with sensitivity in the visual, infrared and/or near-infrared range;
- at least one spectrograph composed of an optical dispersing element such as a grating or prism to split the light into many narrow, adjacent wavelength bands, said spectrograph being placed before the camera and being tunable so that specific wavebands can be selected and transmitted to the camera in a predetermined sequence;
- at least one suitable optical lens;
- at least one light source with suitable spectral composition in the near infrared range to illuminate said plant;

computer hardware elements and connections to the different previous elements;

dedicated software elements for driving signal outputs and inputs from and to the hardware elements, and automatically perform the different steps of the method described in any one of embodiments 1 to 24 and 39 to 41.

Embodiment 34

Use of an apparatus according to any one or more of embodiments 27 to 33 for evaluating the effects of a treatment on a plurality of plants.

Embodiment 35

Use of an apparatus according to any one or more of embodiments 27 to 33 in the method of any one of the embodiments 1 to 24 and 39 to 41.

Embodiment 36

Use of an apparatus according to any one or more of embodiments 27 to 33 in a method for comparing the effects of different growth conditions of plants in relation to the effects of a treatment on a plurality of plants.

Embodiment 37

Use of an apparatus according to any one or more of embodiments 27 to 33 in a method for phenotyping and/or metabolic profiling, for selecting the most desired genotypes based on phenotype or metabolite scoring in the evaluation of the effects of a treatment on a plurality of plants.

Embodiment 38

Use of an apparatus according to any one or more of embodiments 27 to 33 in a method for testing the effects of treatment of plants, such as one or more of: testing of specific fertilizers and/or nutrients; testing of specific biocides, the selection and/or breeding of plants having one or more desired properties in response to the effects of a specific treatment; the testing of the effect and/or effectiveness of specific treatments, such as 1, 2, 3, 4, 5, 6, 7, 8, 9, 10, 11, 12, 13, 14, 15, 16, 17, 18, 19, 20 treatments of the plants or plant specimens with fertilizers, nutrients and/or biocides.

Embodiment 39

Method of embodiment 2, wherein said unique identifier 180 communicates with unique identifier reader 181.

Embodiment 40

Method according to any or more of embodiments 1 to 19, wherein the treatment is on above-ground plant parts.

Embodiment 41

Method according to embodiment 22, wherein the defined solution comprises growth promoting substances, either as chemical compound or as a microbial suspension.

Embodiment 42

Apparatus according to any one or more of the embodiments 25 to 29, wherein said treatment system 150 comprises a spraying system 151 suitable for spraying above-ground plant parts.

In order that the invention may become more clear there now follows a description to be read with the accompanying schematic drawings of apparatuses and methods according to the invention and their use in a process according to the invention selected for description to illustrate the invention by way of example. The examples are by way of illustration alone and are not intended to completely define or to otherwise limit the scope of the invention.

Figure 1A:
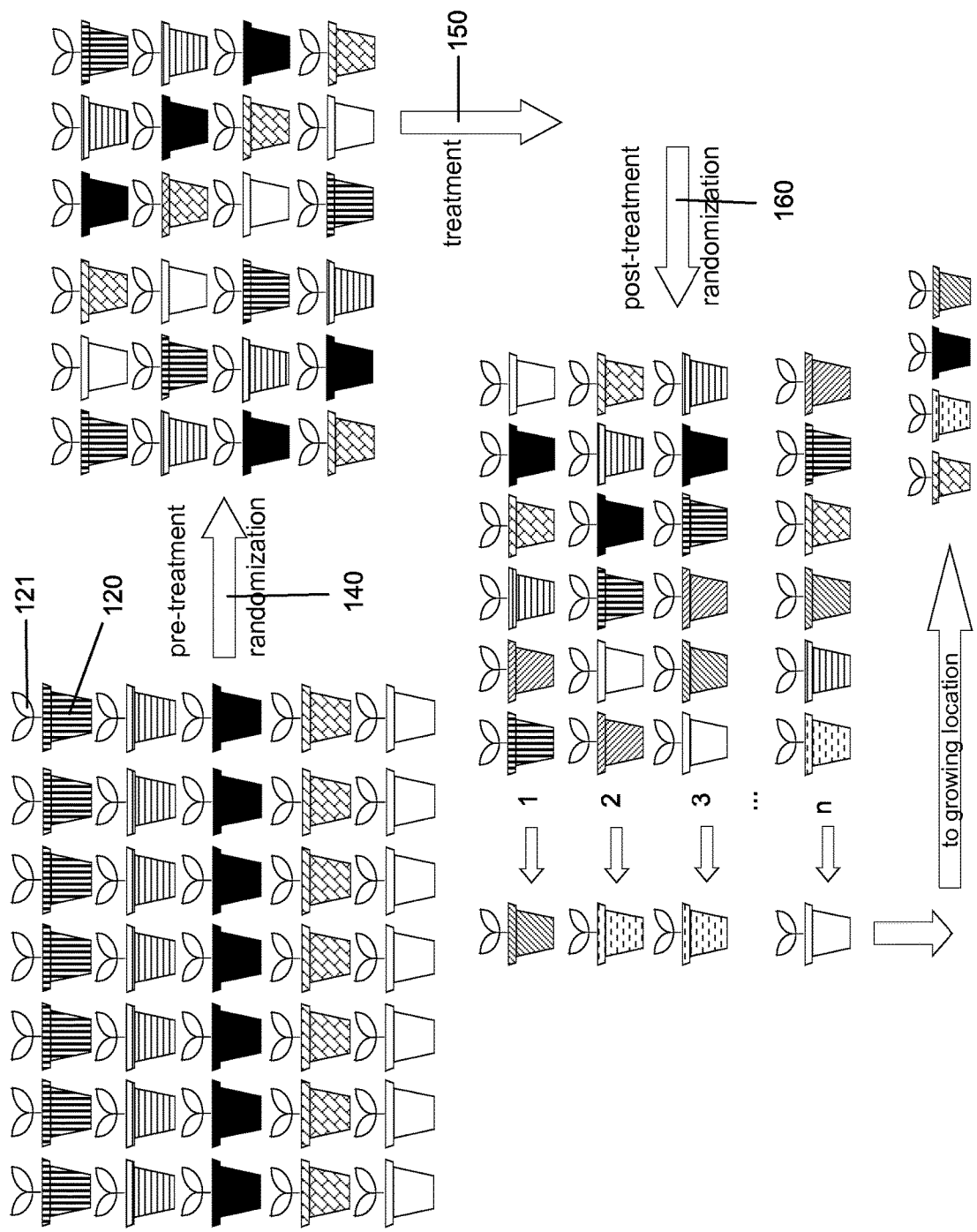
FIG. 1 is a schematic view of one embodiment of a method and apparatus for high throughput evaluation of the effects of a treatment on a plurality of plants.

110: apparatus for high throughput treatment of a plurality of plants
120: plant container
121: plant
130: container moving system (not shown)
140: pre-treatment randomisation system
141: pre-spraying randomisation system
150: treatment system
151: spraying system
152: watering system
160: post-treatment randomisation system
161: post-spraying randomisation system
170: drying system
180: unique identifier (not shown)
181: unique identifier reader
190: imaging system
191: detector (not shown)
192: image
193: image analysis device
200: control system

EXAMPLES

FIG. 1A is an example of a method and apparatus for high throughput evaluation of the effects of a treatment on a plurality of plants. The plants 121 are growing in plant containers 120 at a growing location, in this example a greenhouse. Such greenhouse provides to the plant containers an environment of controlled climatic conditions with controlled supply of nutrients and feed water. But it goes without saying that the plants in the plant containers in such greenhouse are influenced by variations in the growth environment (micro-climate variations) caused by variations in, for example, temperature, humidity, light, nutrient, and water supply, which are depending on the location of the plant container in the greenhouse (position effects). A plant in a plant container at the outer side of the greenhouse or of a growth table is exposed to a different micro-environment than a plant in a plant container at the centre of the greenhouse or at the centre of a group of plants (edge effects). Typically, the plant containers are set-up in rows or on tables in such greenhouse and problems of environment-associated phenotype and/or metabolite components are dealt with by moving the plant containers to another spot in the greenhouse. Most of the commercially available systems work, in case of a row set-up, in a first-in, first-out or a first-in, last out way. This is not providing a real randomisation of the plants or plant containers. This is overcome by the system and method of the invention.

The apparatus 110 (not depicted) comprises a container moving system 130 (not depicted) to move the plant containers 120. The plant containers 120 are moved from the growing location into apparatus 110. The apparatus further also comprises a pre-treatment randomisation system 140 to randomise the plant containers; a treatment system 150; and a post-treatment randomisation system 160. In the method of the invention each of the plant containers 120 move into the apparatus by the container moving system 130 and to the pre-treatment randomisation system 140. The plant containers are then randomised by that pre-treatment randomisation system 140, which used the originating cultivation location as the randomising factor. Thereafter the containers 120 move further on the container moving system 130 to the treatment system 150 which then treats the plants 121 in the plant containers. Thereafter, the plant containers 120 containing the treated plants move via the container moving system 120 to the post-treatment randomisation system 160 which performs a second randomisation of the plant containers, but now the treatment is the randomising factor. Thereafter the plant containers are moved out of the apparatus by the container moving system. Preferably, the plant containers are then moved to a plant growing location, such as a greenhouse or screenhouse. Depending on the treatment, the effect of the treatment on the plants in the plant containers is evaluated immediately or after a certain time after the plant containers left the apparatus of the invention. Such evaluation can be done visually by scoring the plants at the plant growing location or can be done in an automated way. Such automation might entail imaging the plants at the growing location from above the plants or can be performed by bringing the plant containers to an imaging system, as e.g. described in WO2010/031780, where the plants are imaged.

Figure 1B:
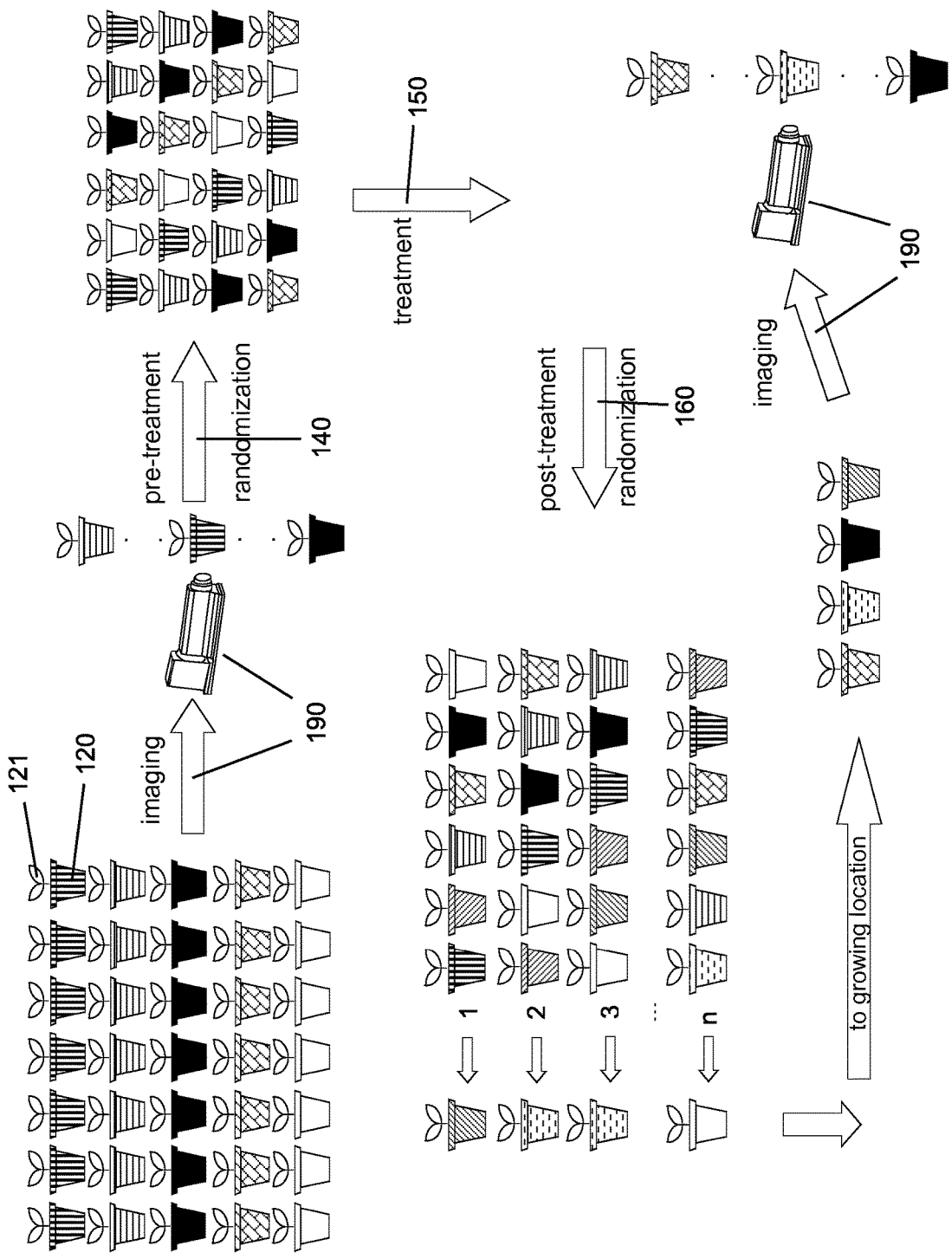

In the exemplary embodiment of FIG. 1B, the plant containers are imaged before the pre-randomisation step and after treatment and post-treatment randomization. This second imaging can be done immediately after the randomization or only after some time wherein the plants had the chance to develop the (full) effect of the treatment at the growing location. One or more characteristics of the plant is measured from the images by appropriate software.

If desired, algorithms may be used to evaluate the measured one or more characteristics.

The imaging system 190 comprises a detector 191. In this example of FIG. 1B, the detector 191 is a digital camera.

The imaging system of FIG. 1B may further comprise at least one image analysis device 193 (not shown). The image analysis device 193 may be adapted to perform at least one image analysis of at least one of the images 192, preferably the image analysis device 193 may be adapted to generate at least one characteristic or trait of an imaged plant. The term generate according to the present invention may refer to deriving e.g. from the image analysis.

The apparatus of the invention may further also comprise an identifier reader 181 (not shown) to identify an identifier linked to a plant in a plant container or even a group of plants in a plant container. Such a reader can be a barcode reader, a transponder reader and/or an RFID reader. In a preferred embodiment, the apparatus further comprises at least one electronic code reading device to identify an identifier linked to said plant.

The apparatus further may have at least one database (not shown) for recording data regarding the plant, the treatment and the effect of the treatment, i.e. the one or more characteristics of the plant after treatment and or the difference in the one or more characteristics before and after treatment of a particular plant. The data preferably may be at least one of the following: at least one image of the plant aboveground and/or belowground; at least one characteristic or trait derived from at least one image of the plant; at least one or more characteristic derived from metabolite analysis of a sample taken from a plant, information from the identifier; information on the treatment; information on the time after treatment when determination of the effect takes place. As outlined above, the at least one characteristic or trait may comprise one or more parameters characterizing the phenotype of the plants. In a preferred embodiment, the methods of the present invention can be used to detect any characteristics of the plants that can be measured by imaging. The images may be taken from aboveground plant parts and/or or plants roots. The aboveground plant parts may be one or more of shoots, leaves, tillers, inflorescence, flowers, seeds. In one preferred embodiment, the characteristic is one or more of a quantitative trait, a biochemical trait and a morphological trait. In an even more preferred embodiment, the biochemical trait is selected from the group consisting of oil composition, protein composition, carbohydrate composition, amino acid composition, fibre composition, oil content, protein content, carbohydrate content, starch content, amino acid content, secondary metabolite content, fibre content, dry weight and water content. In another even more preferred embodiment, the morphological trait is selected from plant architecture, plant size, plant shape, branching, aboveground biomass, plant colour, plant growth rate, leaf surface texture, plant weight, plant integrity, leaf integrity, leaf colour, leaf shape, leaf size, leaf growth rate, belowground biomass, root growth rate, root thickness, root length, root branching, root anchorage, inflorescence architecture, flower size, flower shape, flower colour, flower surface texture, flower weight, flower integrity, endosperm size, germ size, seed shape, seed size, seed colour, seed surface texture, seed weight, seed density, and seed integrity. As used herein, integrity is correlated to susceptibility or resistance to any one of diseases, insect infestation, and fungal infestation. In an alternative preferred embodiment, the quantitative trait is selected from amount of (green) leaves, amount of roots, such as amount of hairy roots and/or branched roots, amount of florets, amount of seeds, amount of empty seeds, amount of branching, weight of seeds, total weight of seeds and/or fill rate. However, other types of parameters and/or combinations of the named parameters and/or other parameters may be possible, e.g. aboveground biomass per plant and per area; belowground biomass per area; content of oil, starch and/or protein in aboveground biomass (e.g., seeds or vegetative parts of the plant); number of flowers (florets) per plant; or modified architecture, such as increase stalk diameter, thickness or improvement of physical properties (e.g. elasticity).

The apparatus furthermore may comprise a control system 200 which may be adapted to control and/or to drive the imaging system 190 and/or container moving system 130 and/or the image analysis device 193 and/or the reader 181 and/or the database and/or a power supply. The control system 200 may comprise a computer and electrical and/or signal connectors, preferably electrical lines and interfaces.

Images 192 taken with the imaging system 190 can be processed on-line using imaging analysis software to extract information on the one or more characteristics of the plant and preferably, the processed data as well as the images get linked to a unique identifier and even more preferably, downloaded to a computer.

Figure 2A:
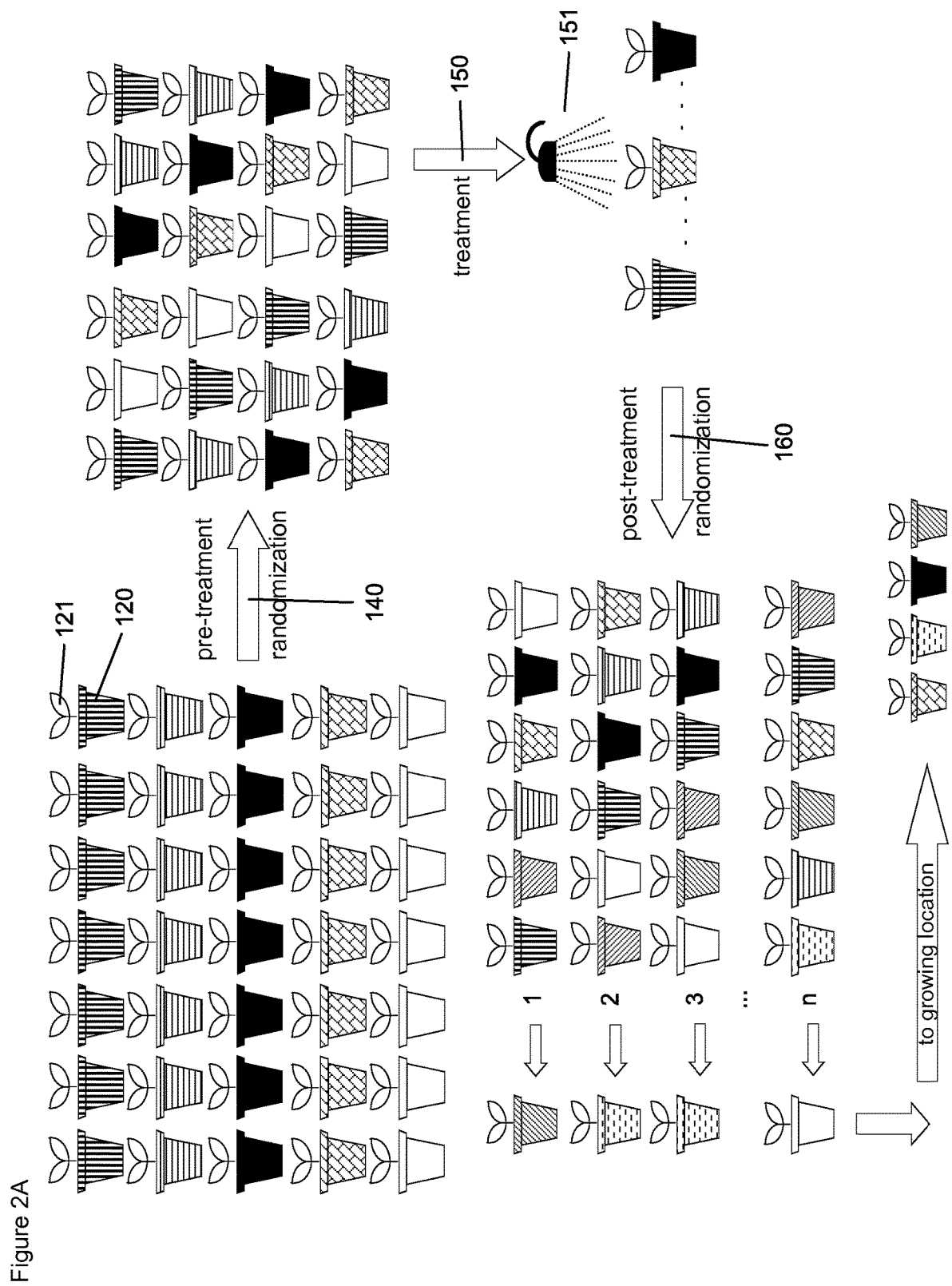
FIGS. 2A and 2B is a schematic view of a method and apparatus for high throughput evaluation of the effects of a spraying treatment on a plurality of plants.
Figure 2B:
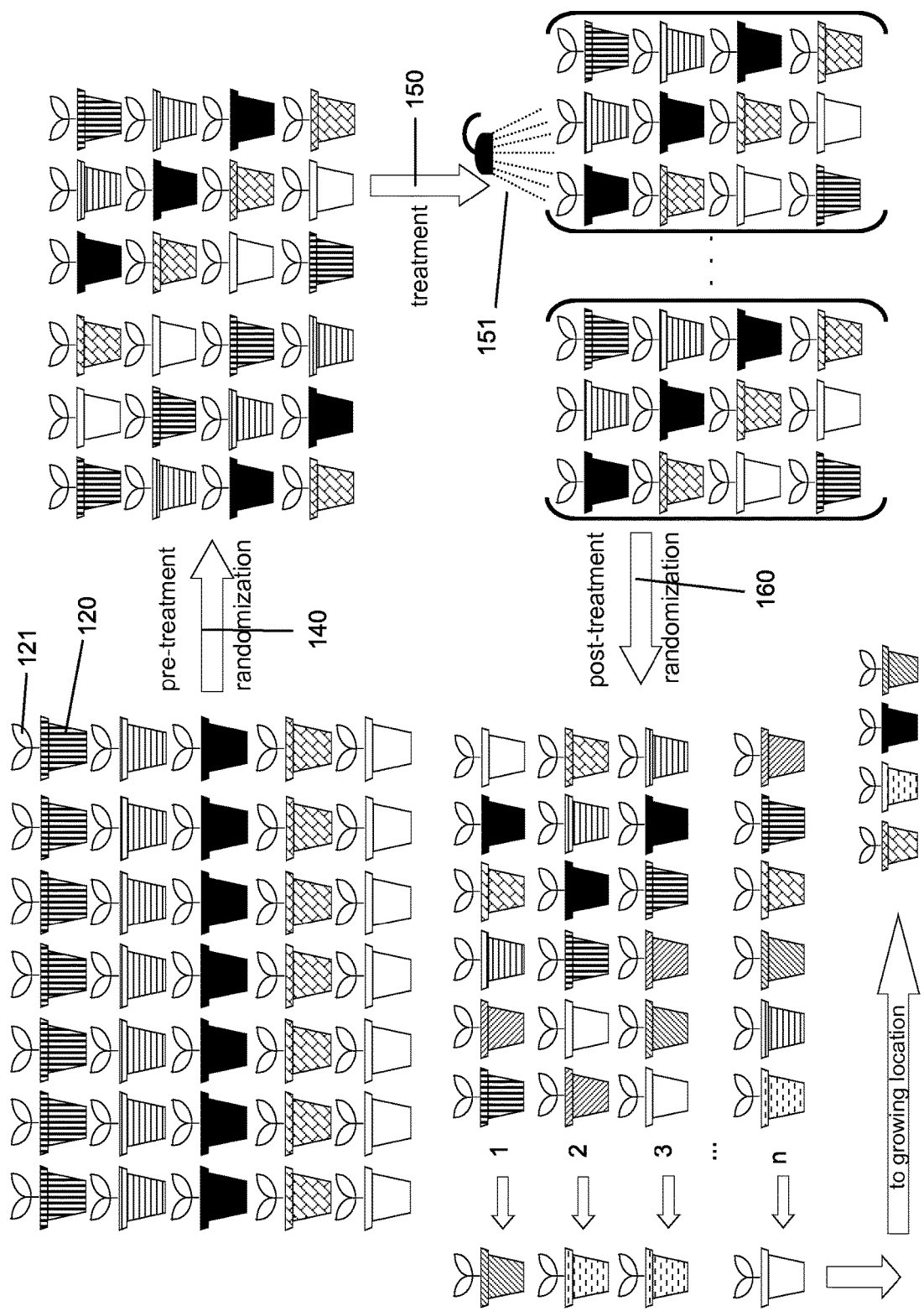

In a third exemplary embodiment, as shown in FIG. 2A, the apparatus and method is the same as the one described in FIG. 1A, but the treatment is a spraying treatment 151. The spraying treatment can be done on the at least one plant 121 in the plant containers 120, on a one by one plant container basis, or the spray treatment 151 can be done in block of multiple plants in containers. In the exemplary embodiment of FIG. 2B, the block consists of 12 plant containers. But the skilled person will acknowledge that any amount of plant containers can be taken to form a block for the concurrent spraying of the plant containers. Spraying can be done top-down and/or on the side of the plant to be treated. As described above, depending on the treatment, the effect of the treatment on the plants in the plant containers is evaluated immediately or after a certain time after the plant containers left the apparatus of the invention. Such evaluation can be done visually by scoring the plants at the plant growing location or can be done in an automated way. Such automation might entail imaging the plants at the growing location from above the plants or can be performed by bringing the plant containers to an imaging system, as e.g. described in WO2010/031780, where the plants are imaged.

Figure 3A:
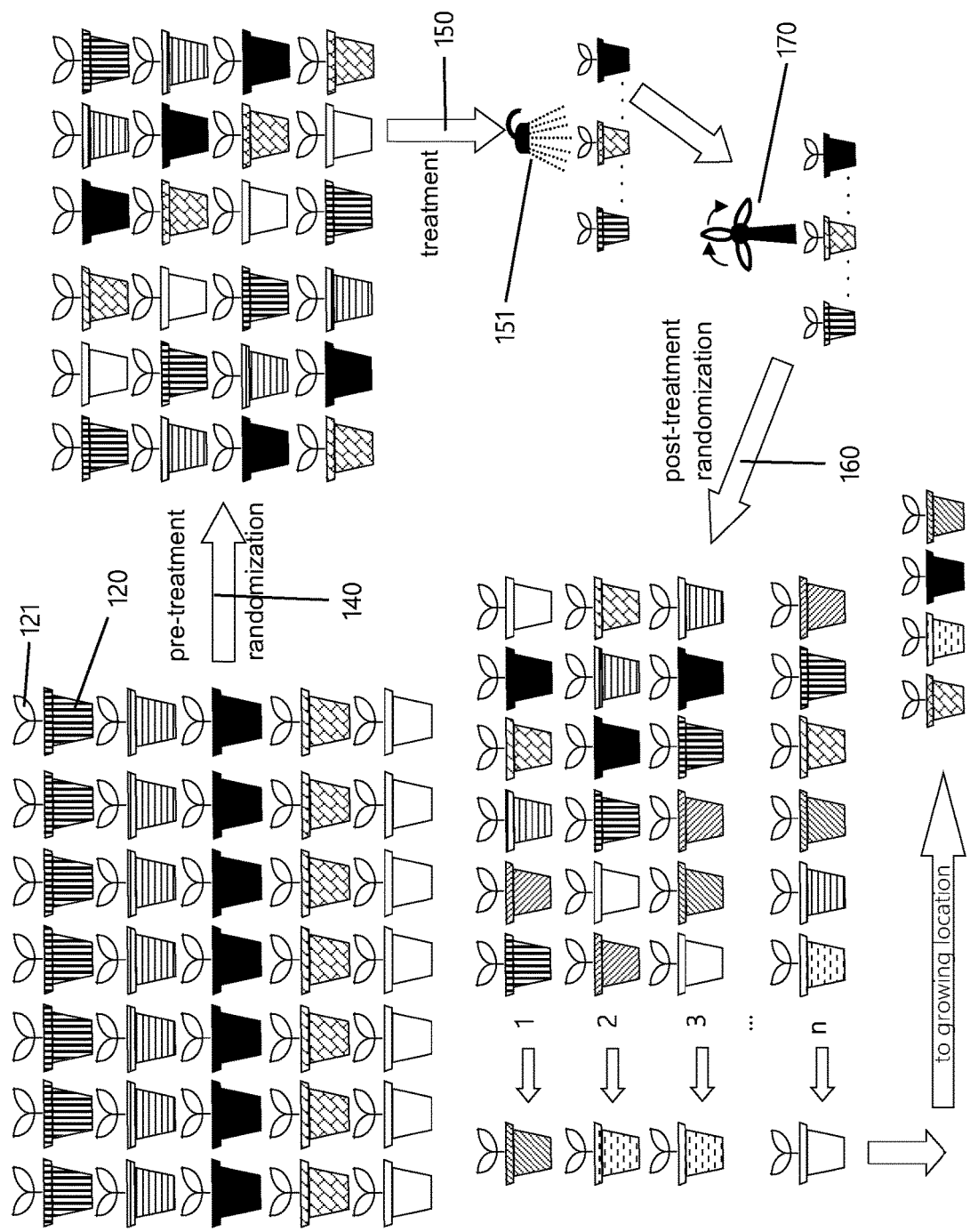
FIGS. 3A and 3B shows a schematic view of a method and apparatus for high throughput evaluation of the effects of a combined spraying and drying treatment on a plurality of plants.
Figure 3B:
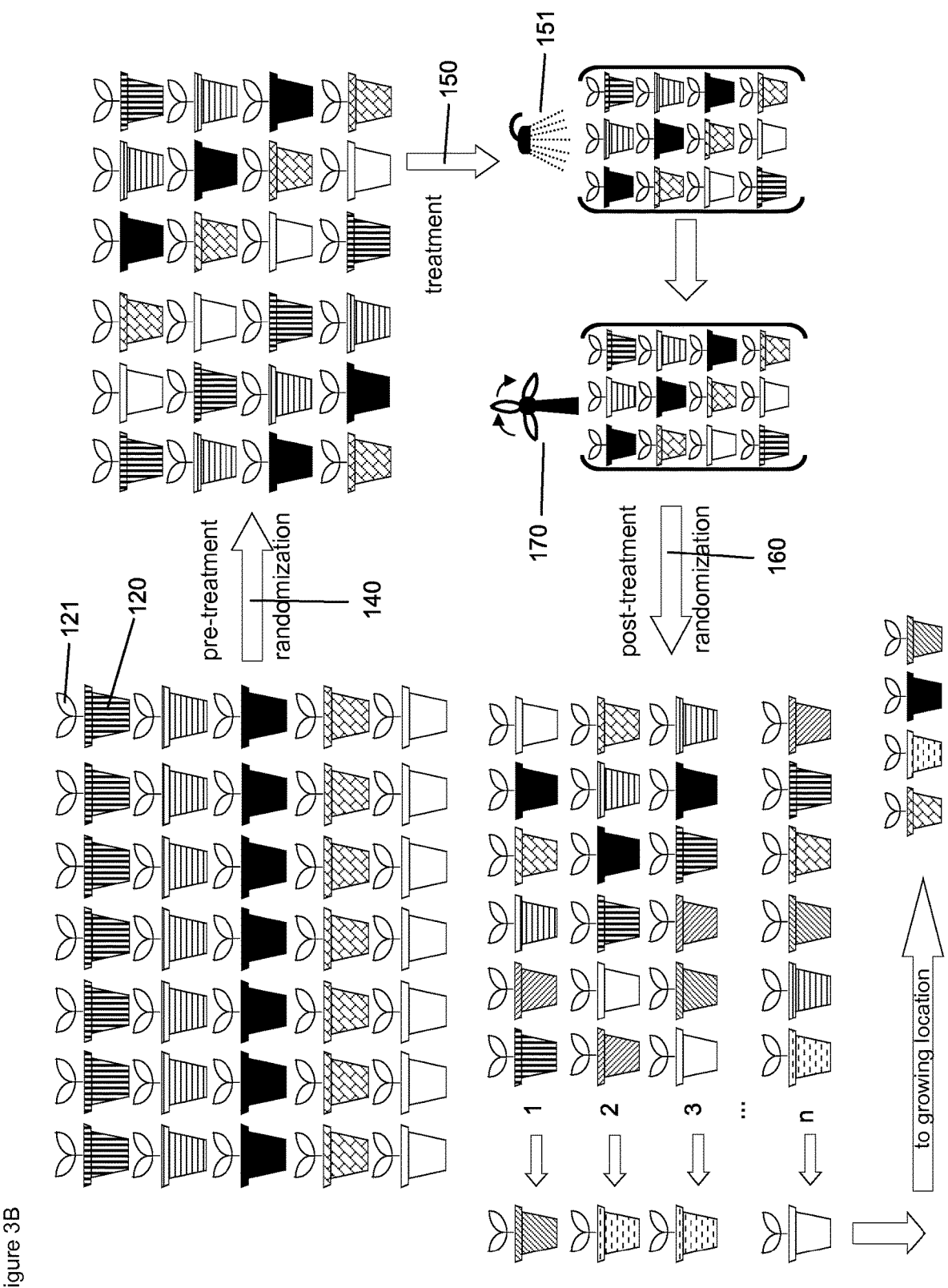

FIG. 3A shows a further exemplary embodiment, based on the example as shown in FIG. 2A, wherein the method further also comprises a step of drying 170 of the plants in the plant containers. The apparatus 110 therefore comprises a drying tunnel or similar device. The spraying and drying treatment can be done on the at least one plant 121 in the plant containers 120, on a one by one plant container basis, or the spray treatment 151 can be done in block. In the exemplary embodiment of FIG. 3B, the block consists of 12 plant containers. But the skilled person will acknowledge that any amount of plant containers can be taken to form a block for the concurrent spraying and drying of the plant containers. As described above, depending on the treatment, the effect of the treatment on the plants in the plant containers is evaluated immediately or after a certain time after the plant containers left the apparatus of the invention. Such evaluation can be done visually by scoring the plants at the plant growing location or can be done in an automated way. Such automation might entail imaging the plants at the growing location from above the plants or can be performed by bringing the plant containers to an imaging system, as e.g. described in WO2010/031780, where the plants are imaged.

The skilled person will understand that also an imaging step as described in FIG. 1B can be added to the method of FIGS. 2A, 2B, 3A, 3B. The plant containers are than imaged before the pre-randomisation step and after treatment and post-treatment randomization. This second imaging can be done immediately after the randomization or only after some time wherein the plants had the chance to develop the (full) effect of the treatment at the growing location. The one or more characteristics of the plant is measured from the images by appropriate software. If desired, algorithms may be used to evaluate the measured one or more characteristics.

Figure 4:
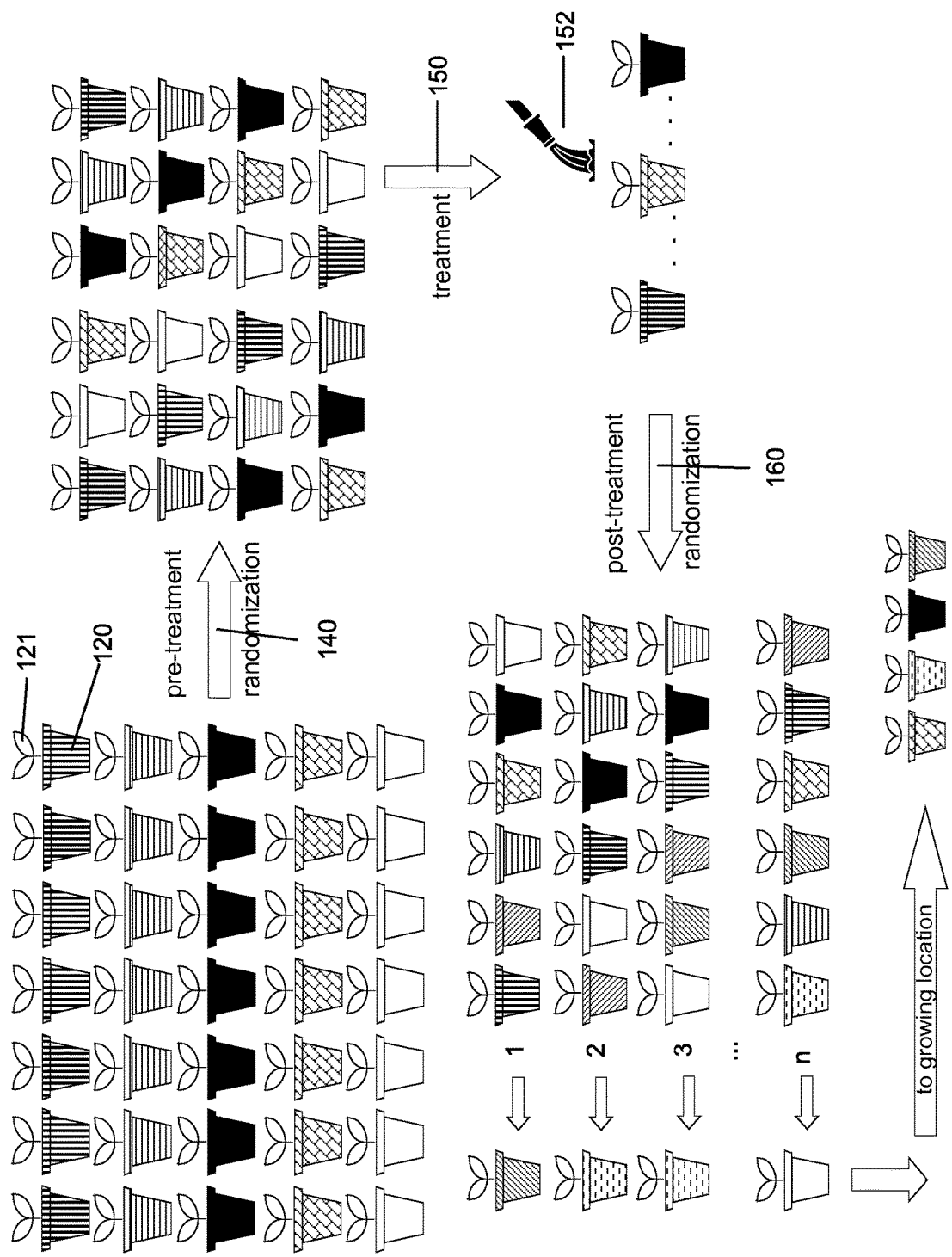
FIG. 4 shows a schematic view of a method and apparatus for high throughput evaluation of the effects of a watering treatment on a plurality of plants.

FIG. 4 shows a further exemplary embodiment wherein the apparatus and method is the same as the one described in FIG. 1A, but the treatment is a watering treatment 152. The watering treatment will be a specific solution provided to the plant containers and this solution will comprise specific nutrient solution or biocide solution, or any other solution or suspension that affects plant growth. Such defined solution can then be provided via watering to at least one plant container 120, on a one by one plant container basis, or the watering treatment 151 can be done in block. The skilled person will acknowledge that any amount of plant containers can be taken to form a block for the concurrent watering of the plant containers. As described above, depending on the treatment, the effect of the treatment on the plants in the plant containers is evaluated immediately or after a certain time after the plant containers left the apparatus of the invention. Such evaluation can be done visually by scoring the plants at the plant growing location or can be done in an automated way. Such automation might entail imaging the plants at the growing location from above the plants or can be performed by bringing the plant containers to an imaging system, as e.g. described in WO2010/031780, where the plants are imaged.

The skilled person will understand that also an imaging step as described in FIG. 1B can be added to the method of FIG. 4.

In a preferred embodiment, the imaging system 190 comprises the following:
at least one digital camera with sensitivity in the visual, infrared and/or near-infrared range;
at least one spectrograph composed of an optical dispersing element such as a grating or prism to split the light into many narrow, adjacent wavelength bands, said spectrograph being placed before the camera and being tunable so that specific wavebands can be selected and transmitted to the camera in a predetermined sequence;
at least one suitable optical lens;
at least one light source with suitable spectral composition in the near infrared range to illuminate said plant with light,
computer hardware elements and connections to the different previous elements and
dedicated software elements for driving signal outputs and inputs from and to the hardware elements, and automatically perform the different steps of the method described herein.

Such imaging is often referred to in literature as imaging spectroscopy, which is the simultaneous acquisition of spatially co-registered images in many spectrally contiguous bands. In the art, the wording "hyper spectral image cubes" are described as multichannel images being composed of many spectrally contiguous spectral bands of relatively narrow bandwidths (e.g., 1-10 nm), whereas, "multi-spectral" images are usually fewer (e.g., 5-10) bands of relatively large bandwidths (e.g., 70-400 nm).

The imaging system at least comprises a detector 191. Such detector may be a hyperspectral camera. In another preferred embodiment, the imaging system comprises a multispectral camera.

In another exemplary embodiment, the method according to the invention further involves the following steps:
Collection of digital images of individual plants before and/or after treatment. One image of each individual plant is collected by use of a normal RGB colour camera.
Generation of one or more characteristics using appropriate software.
Determination of the pixels belonging to the plant organs, as opposed to the non-plant background. This is achieved using standard image processing algorithms, such as intensity thresholding, in which the pixel values differing from predetermined background values are considered as belonging to the plant object.

Determination of pixels belonging to the one or more characteristics, as opposed to the rest of the plant organs. This is achieved by standard image processing algorithms, such as morphological segmentation, in which objects are identified as e.g. seed or non-seed, flower, leaf, when their geometrical properties correspond to predefined specifications.

Calculation of the metric properties per each individual object identified in the image, based on the combined properties of all individual pixels constituting each object. These properties include amongst other physical dimensions in the 2 dimensional space and amount of plant characteristics.

In a further exemplary embodiment, the method of the invention involves the following steps:

Identification of each plant or group of plants being measured by means of unambiguous coding system. Ideally the coding system is of a type that can be read electronically, e.g. barcode, or transponder tag.

Collection of digital images of individual plants. Many images of the same individual plants are collected at many different narrow wavebands in the near infrared range of the light spectrum, namely between 900 and 1700 nm.

Generation of hyper-spectral image cube by alignment of the images recorded at the different wavelengths in order to generate a 3 dimensional image comprising 2 spatial dimensions (x, y) and 1 spectral dimension (z). From such images, a spectrum of light absorption for each pixel in the two-dimensional space can be generated.

Estimation of the amount of dry matter and basic chemical composition corresponding to each pixel, based on a customary predictive mathematical model combining the weighted contributions of the different wavelengths at each pixel.

Determination of the pixels belonging to the plant organs, as opposed to the non-plant background. This is achieved using standard image processing algorithms, such as intensity thresholding, in which the pixel values differing from predetermined background values are considered as belonging to the plant object.

Determination of pixels belonging to the one or more characteristics, as opposed to the rest of the plant organs. This is achieved by standard image processing algorithms, such as morphological segmentation, in which objects are identified as e.g. seed or non-seed, leaf, flower, when their geometrical properties correspond to predefined specifications.

Calculation of the metric properties per each individual object identified in the spectral image, based on the combined properties of all individual pixels constituting each object. These properties include: physical dimensions in the 2 dimensional space, estimated dry weight, and estimated chemical composition.

The invention claimed is:

1. Method for high throughput evaluation of the effects of a treatment on a plurality of plants said method comprising following steps:
   providing a plurality of plant containers 120 wherein at least one plant 121 is growing
   providing a container moving system 130 to move said plant containers
   providing a pre-treatment randomisation system 140 to randomise said plant containers
   providing a treatment system 150, and
   providing a post-treatment randomisation system 160,
   wherein each of said plant containers 120 moves by said container moving system 130 to said pre-treatment randomisation system 140,
      said pre-treatment randomisation system 140 randomising the plant containers 121,
      said container moving system 130 then moving said containers 121 to said treatment system 150,
      said treatment system 150 providing at least one treatment,
      thereafter said container moving system 130 moving said containers to said post-treatment randomisation system 160,
      said post-treatment randomisation system 160 performing a second randomisation of said plant containers,
      said container moving system 130 moving said containers 120 to a growing location and then evaluating the effect of the treatment.

2. Method according to claim 1, wherein said plant in said plant in said plant container is linked to a unique identifier 180.

3. The method according to claim 2, said method further providing at least one imaging system 190, wherein said plant containers pass through said imaging system 190 before and/or after said treatment.

4. The method according to claim 3, wherein said imaging system 190 is imaging one or more characteristics of said plant and analyzing the images for the one or more characteristics of the plant by computer processing and associating the resulting information with the unique identifier 180 information for said plant 121.

5. The method of claim 4, wherein the one or more characteristics comprises one or more of an observable physical manifestation of the plant, a phenotypic trait, a metabolic trait, color, greenness, yield, growth, biomass, maturity, a transgenic trait, flowering, nutrient use, water use, or effects of disease, pests, and/or stress.

6. Method according to claim 4, said method further comprising a step analyzing the resulting information for the one or more characteristics of the one or more plant to determine the impact of the treatment.

7. The method of claim 1, wherein the plurality of plants comprise one or more transgenic plants.

8. Method according to claim 1, wherein the treatment is a foliar spraying treatment.

9. Method according to claim 8, said method further providing a drying system 170, said method further comprising a step wherein the plant containers pass a drying system after the foliar spraying treatment.

10. Apparatus for high throughput application of a treatment on a plurality of plant containers 120 wherein at least one plant 121 is growing, said apparatus comprising:
   a container moving system 130 to move said plant containers;
   a pre-treatment randomisation system 140 to randomise said plant containers
   a treatment system 150, and
   a post-treatment randomisation system 160,
   wherein each of said plant containers 120 moves into said apparatus by said container moving system 130 to said pre-treatment randomisation system 140, the plant containers being randomised by said pre-treatment randomisation system 140 before moving further on said container moving system 130 to said treatment system 150 wherein said plant containers 120 are treated, the plant containers 120 then move via the container moving system 130 to the post-treatment randomisation system 160, the post-treatment randomization system 160 providing a second randomisation of said plant containers and thereafter the plant containers 120 being moved by said container moving system 130 out of said apparatus.

11. Apparatus according to claim 10 wherein said apparatus further comprises a unique identifier reader 181.

12. Apparatus according to claim 10, said apparatus further comprising at least one imaging system 190.

13. Apparatus according to claim 10, wherein said treatment system 150 comprises a foliar spraying system 151.

14. Apparatus according to claim 13, wherein said apparatus further comprises a drying system 170.

* * * * *